United States Patent [19]

Boyles

[11] Patent Number: 4,705,507
[45] Date of Patent: Nov. 10, 1987

[54] ARTERIAL CATHETER MEANS

[76] Inventor: Paul W. Boyles, 407 Glasgow Rd., Cary, N.C. 27511

[21] Appl. No.: 856,206

[22] Filed: Apr. 28, 1986

Related U.S. Application Data

[63] Continuation-in-part of Ser. No. 606,255, May 2, 1984, Pat. No. 4,592,340.

[51] Int. Cl.⁴ ............................................. A61M 29/00
[52] U.S. Cl. ................................... 604/101; 604/247; 128/1 D
[58] Field of Search ............................. 604/53, 96–98, 604/101–102, 247; 3/2; 128/1 D, 207.15

[56] References Cited

U.S. PATENT DOCUMENTS

| 15,192 | 6/1856 | Peale | 623/2 |
|---|---|---|---|
| 3,173,418 | 3/1965 | Baran | 604/101 |
| 3,331,371 | 3/1965 | Rocchi | 604/96 |
| 3,592,184 | 7/1971 | Watkins | 604/247 |
| 3,671,979 | 6/1972 | Moulopoulos | 604/247 |
| 3,995,617 | 12/1976 | Watkins et al. | 604/247 |
| 4,423,725 | 1/1984 | Baran et al. | 128/207.15 |
| 4,592,340 | 6/1986 | Boyles | 128/1 D |

Primary Examiner—C. Fred Rosenbaum
Assistant Examiner—Gene B. Kartchner
Attorney, Agent, or Firm—Mills & Coats

[57] ABSTRACT

An arterial catheter of the multi-lumen type having an inflatable balloon portion to wedge the catheter in place against the arterial wall. Multi-infusions are allowed through the segmented multi-lumens. This catheter is so designed to allow blood to flow in the arterial system with the catheter in place. During diastolic phases, the blood flow will be closed off with movable plastic valves.

1 Claim, 12 Drawing Figures

4,705,507

ARTERIAL CATHETER MEANS

This application is a continuation-in-part of the parent application, Ser. No. 606,255, filed May 2, 1984 now Pat. No. 4,592,340.

FIELD OF INVENTION

This invention relates to medical appliances and more particularly to multi-infusion catheters.

BACKGROUND OF INVENTION

Both venous and arterial multi-lumen catheters have been used for various procedures by the medical profession. Also, intra-aortic balloons have been used as pump counterpulsation as an accepted modality for providing diagnostic augmentation and afterload reduction in patients requiring temporary cardiac support.

The multi-lumen catheters, whether venous or arterial, all share the common problem of maintaining proper position within the respective vein or artery. Also, these multi-lumen catheters share the same limitations of being useful only for infusion or diagnostic purposes.

BRIEF DESCRIPTION OF INVENTION

After much research and study into the above-mentioned problems, the present invention has been developed to provide an arterial catheter which allows blood flow in the arterial system to occur during the systolic phase of the cardiac cycle but not during the diastolic phase, the flow is closed by means of movable plastic valves inside the main catheter. The catheter of the present invention is held in place by an inflated means wedged against the arterial wall and multi-infusions are provided through additional catheter lumens thereby allowing segmented infusion of radio opaque dyes, enzymes, drugs and the like during the diastolic phase.

In view of the above, it is an object of the present invention to provide an arterial catheter means which allows blood flow in the arterial system during the systolic phase of the cardiac cycle but effectively stops the flow of blood during the diastolic phase.

Another object of the present invention is to provide a means for allowing blood to flow in the arterial system during the systolic phase of the cardiac cycle but automatically blocks backflow during the diastolic phase.

Another object of the present invention is to provide an arterial catheter means which is held in place by an inflated means which wedges against the arterial wall.

Another object of the present invention is to provide means for blocking backflow during the diastolic phase of a cardiac cycle.

Another object of the present invention is to provide a means for segmentally infusing radio opaque dyes, enzymes, drugs and the like during the diastolic cardiac phase.

Other objects and advantages of the present invention will become apparent and obvious from a study of the following description and the accompanying drawings which are merely ilustrative of such invention.

DETAILED DESCRIPTION OF INVENTION

Figure 1:
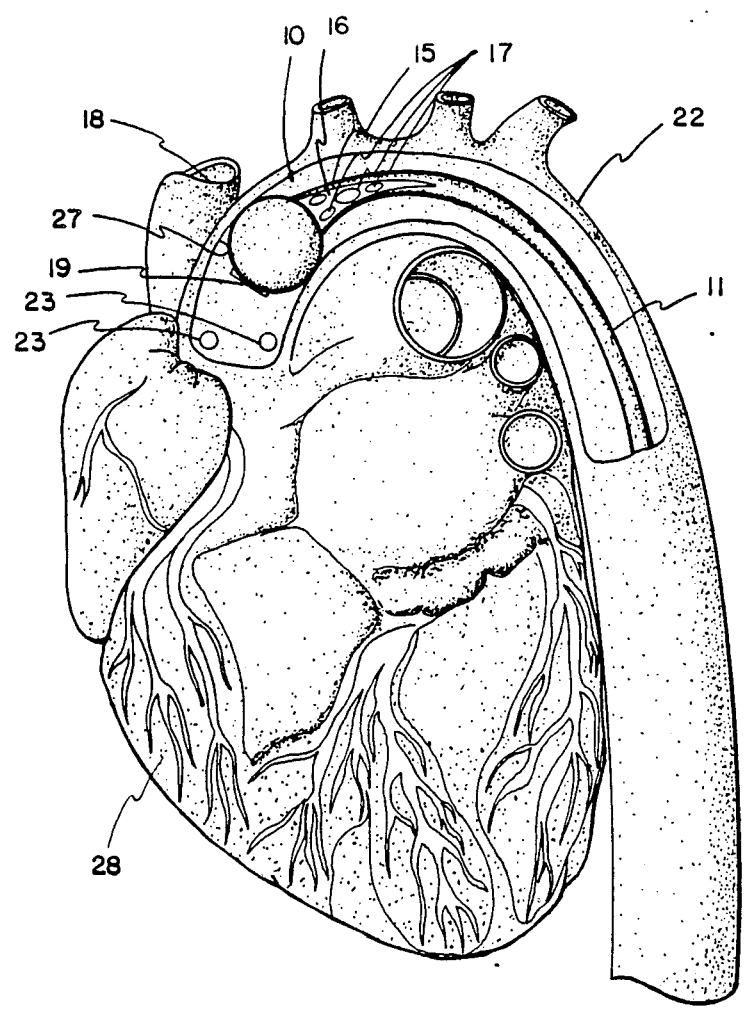
FIG. 1 is a partially cutaway view of the aortic arch of the heart showing the aortic catheter of the present invention in place.

With further reference to the drawings, the arterial catheter means of the present invention, indicated generally at 10, includes a mult-lumen catheter 11 which includes at least three separate and distinct lumens 12, 13 and 14.

The individual lumens divide into the walls of the catheter 11 where the interior end of such catheter enlarges as indicated at 15. The side wall 16 of the enlarged portion 15 has a plurality of openings 17 therein to allow the flow of blood therethrough as will hereinafter be described in greater detail.

An inflatable balloon portion 18 is disposed about the exterior of the outer end of enlarged portion 15 with such enlarged portion passing axially therethrough. The walls of the enlarged portion interior of the balloon portion 18 are, of course, liquid impervious.

Lumen 14 communicates with the interior of balloon portion 18. Since this balloon portion is sealed circumferentially on both ends about enlarged portion 15, such balloon portion can be inflated and deflated by applying positive and negative pressures to the interior thereof through lumen 14. Since the application of positive and negative pressures of this type are well known to those skilled in the art, further detailed discussion of this portion of the present invention is not deemed necessary.

Figure 3:
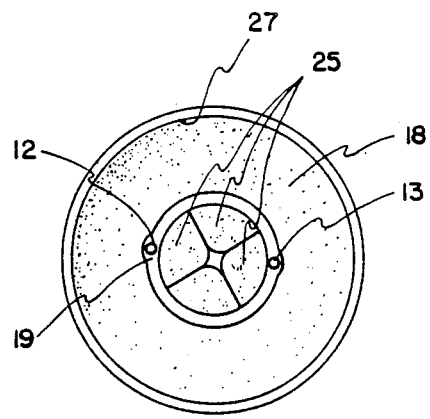
FIG. 3 is a sectional view taken through lines 3—3 of FIG. 2.
Figure 4:
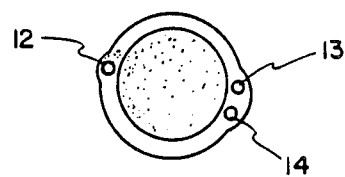
FIG. 4 is a sectional view taken through lines 4—4 of FIG. 2.
Figure 5:
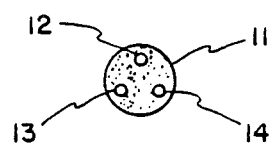
FIG. 5 is a sectional view taken through lines 5—5 of FIG. 2.

The terminal end 19 of enlarged portion 15 exposes lumens 12 and 13 as can clearly be seen in FIG. 3 in order that radio opaque dyes, enzymes, drugs and the like can be segmentally infused during the diastolic phase.

Figure 2:
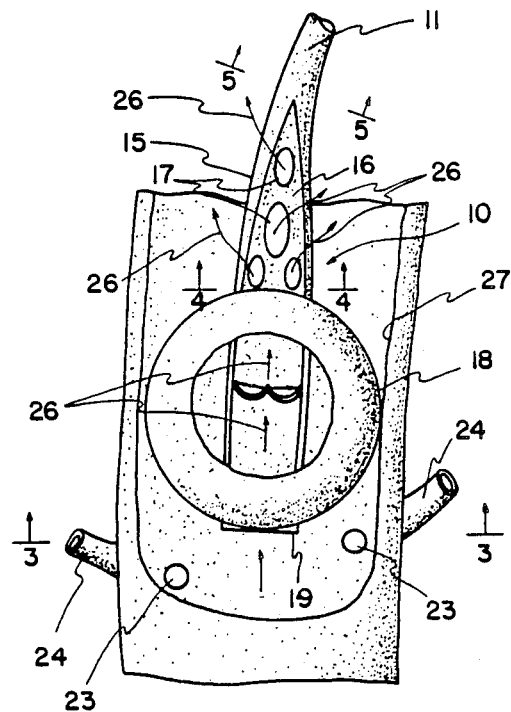
FIG. 2 is an enlarged cutaway view of the catheter of the present invention in the aortic arch.

Catheter valves 15 are provided interiorly of the longitudinal passageway through the balloon portion 18 as can clearly be seen in the cutaway portion of FIG. 2. These catheter valves are preferably made of a plastic-type material which is either non-traumatogenic or are coated with non-traumatogenic material to eliminate the possibility of blood clots forming as blood passes therethrough. Since materials of this type are well known to those skilled in the art, further detailed description of the same is not deemed necessary. The catheter valve 25 acts as a check valve which opens when the heart pumps and then closes thereby restricting blood flow when the heart relaxes.

When it is desired to use the arterial catheter means of the present invention, the terminal end 19 with its associated balloon portion 18 and enlarged portion 15 is inserted preferably into the femoral artery 20 and is passed up through the aorta 21 into the aortic arch 22 of heart 28 to a point adjacent the openings 23 to the coronary arteries 24.

Figure 6:
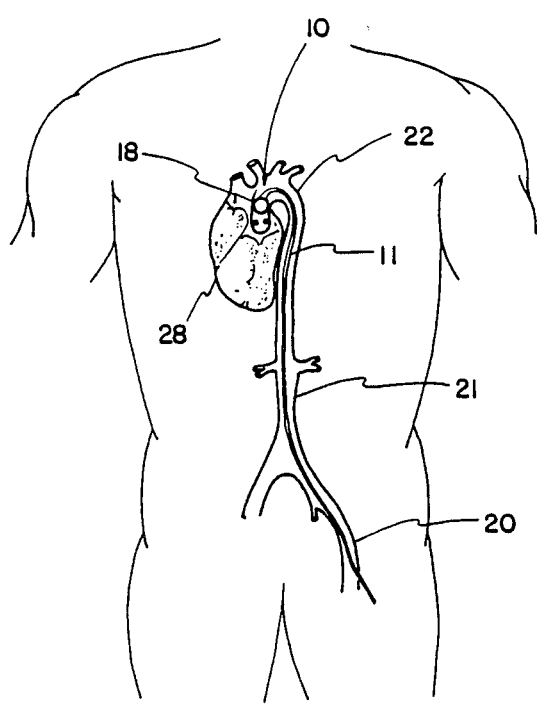
FIG. 6 is a somewhat diagrammatic view illustrating the manner of use of the present invention.
Figure 7:
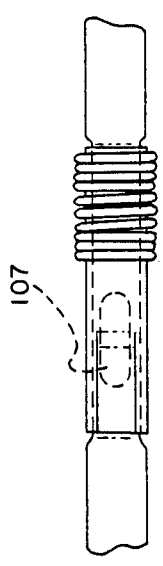
FIG. 7 is a top view of a fragment of the present invention illustrating the construction of the external flap.
Figure 8:
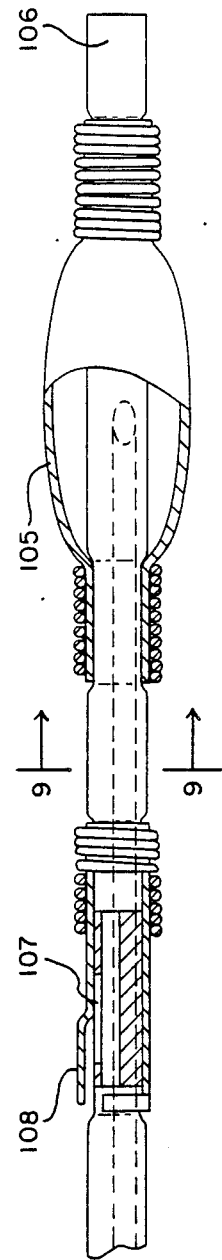
FIG. 8 is a partially cutaway view of the end portion of the present invention.
Figure 10:
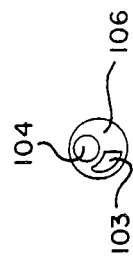
FIG. 10 is an end view of the present invention.

Once the arterial catheter means 10 of the present invention is properly disposed within the aortic arch slightly downstream from the openings 23 of the coronary arteries 24, the balloon portion 18 is inflated through lumen 14 which communicates with the interior thereof. As can clearly be seen in FIGS. 1, 2 and 6, the inflated balloon portion 18 wedges the catheter means in place against the arterial wall 27. As the blood is pumped from the heart 28 during the systolic phase of the cardiac cycle, it flows through the open center of balloon portion 18, past catheter valves 25, out through openings 17 in side wall 16, and intto the arterial system of the patient. During the diastolic phase of the cardiac cycle, the catheter valves 25 automatically close. Since the balloon portion 19 obstructs the remaining portion of the artery, all backflow is effectively eliminated. During this phase, radio opaque dye, enzymes, drugs and the like can be infused through lumens 12 and 13.

Figure 9:
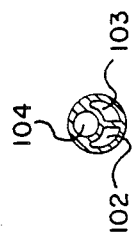
FIG. 9 is a sectional view taken through lines 9—9 of FIG. 8.

With reference now to the modification shown in FIGS. 7 through 10, the multi-lumen catheter is shown therein and indicated generally by the numeral 101. As shown in FIG. 9, the multi-lumen catheter includes two lumens 102 and 103 and a distal intake 104.

The structure of the catheter 101 is similar to the embodiment previously described except that the head portion does not enlarge. An inflatable balloon portion 105 encircles the distal end 106 of the catheter 101. Lumen 102 communicates with the interior of the balloon portion 105 so that the same can be inflated and deflated. Lumen 103 extends through the walls of catheter 101 to the distal end 106 so that enzymes, radio opaque dyes, drugs and the like can be infused during the diastolic phase of the cardiac cycle.

The distal intake 104 extends from the distal end 106 of the catheter 101 a predetermined distance past the balloon portion 105. An opening 107 in the sidewall of the catheter allows blood to flow through the catheter, past the balloon portion 105, and back into the artery. The modification includes the provisions of the external flap 108 covering opening 107 in lieu of the catheter valve 25 of the first described embodiment.

During systole, blood is ejected from the left ventricle with increased pressure. When the catheter is in the root of the aorta and the balloon is inflated and the flow of blood from the left ventricle is forced to flow through intake 104 at the distal end 106 of catheter 101. The pressure of the blood on the underside of flap 108 forces it to open allowing blood to flow through opening 107. During diastole, when blood pressure is reduced, flap 108 returns to its original position closing opening 107. Thus, the back flow of blood during diastole is prevented.

Figures 11, 12:
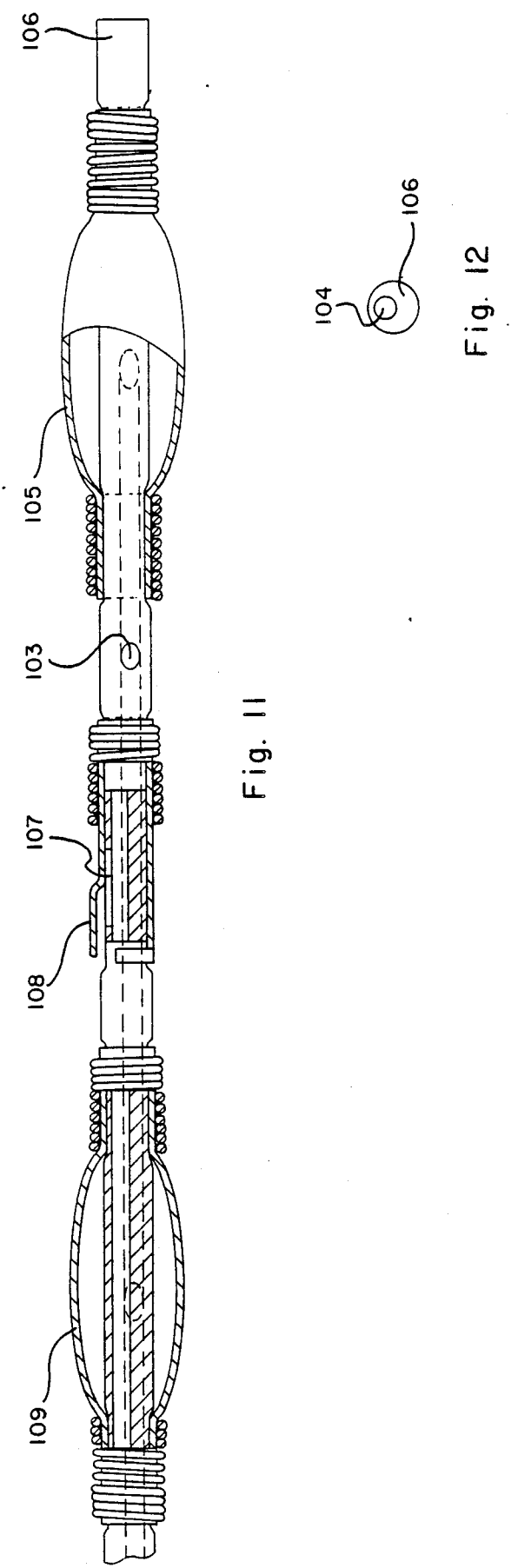
FIG. 11 is a partially cutaway view of the two balloon species of the present invention.
FIG. 12 is an end view of the two balloon species of the present invention.

With reference now to the second modification shown in FIGS. 11 though 13, it is seen that the same includes a second balloon 109 proximate of opening 107. Lumen 103 extends through the wall of catheter 101 to a point between balloons 105 and 109 as is clearly shown in FIG. 10. The two balloon catheter is designed for use in arteries other than the root of the aorta. The two balloons allow for the isolation of the segments of the artery to be treated.

From the above, it can be seen that the present invention has the advantage of providing an arterial catheter means which allows normal blood flow during the systolic phase of the cardiac cycle and yet effectively blocks backflow during the diastolic phase, which allows radio opaque dyes, enzymes, drugs and the like to be segmentally infused during such diastolic phase. The catheter means of the present invention is readily inserted and removed and yet remains stationarily wedged in place during use. This catheter means also is relatively inexpensive to manufacture and yet is highly efficient in operation.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended Claims are intended to be embraced therein.

What is claimed is:

1. An arterial catheter means for insertion into an arterial passage comprising: a flexible, tube-like base member having an intermediate portion and a distal end portion; a first inflatable balloon means encircling said distal end portion of said base member; second inflatable balloon means encircling said intermediate portion; air passage means communicating with said first and second inflatable balloon means; blood flow passage means extending from said distal end portion to an intermediate portion of said base member between said first and second inflatable balloon means; a blood flow outlet formed in said base member between said first and second balloon means, said blood flow outlet communicating between said arterial passage and said blood flow passage; and self-actuating valve means operatively connected to the exterior of said base member for permitting blood to flow through said blood flow passage during systole while arresting flow during diastole.

* * * * *